US011039586B2

(12) United States Patent
Chomet et al.

(10) Patent No.: US 11,039,586 B2
(45) Date of Patent: Jun. 22, 2021

(54) CREATION AND TRANSMISSION OF MEGALOCI

(71) Applicant: Monsanto Technology, LLC, St. Louis, MO (US)

(72) Inventors: Paul S. Chomet, Mystic, CT (US); Jonathan C. Lamb, Wildwood, MO (US); Richard J. Lawrence, Kirkwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 662 days.

(21) Appl. No.: 14/209,731

(22) Filed: Mar. 13, 2014

(65) Prior Publication Data

US 2014/0283166 A1  Sep. 18, 2014

Related U.S. Application Data

(60) Provisional application No. 61/787,894, filed on Mar. 15, 2013.

(51) Int. Cl.
 *A01H 1/02* (2006.01)
(52) U.S. Cl.
 CPC ............... *A01H 1/02* (2013.01); *A01H 1/021* (2021.01)
(58) Field of Classification Search
 None
 See application file for complete search history.

(56) References Cited

U.S. PATENT DOCUMENTS

| | | | |
|---|---|---|---|
| 6,580,019 | B1 | 6/2003 | McElroy et al. |
| 6,750,379 | B2 | 6/2004 | McElroy et al. |
| 7,919,321 | B2 | 4/2011 | Flasinski |
| 2001/0056583 | A1 | 12/2001 | McElroy et al. |
| 2005/0060769 | A1 | 3/2005 | Gilbertson |
| 2008/0178348 | A1 | 7/2008 | Gilbetson |
| 2011/0126310 | A1 | 5/2011 | Feng et al. |
| 2011/0145940 | A1 | 6/2011 | Voytas et al. |
| 2011/0203012 | A1* | 8/2011 | Dotson ............ C12N 15/8213 800/278 |
| 2011/0239315 | A1 | 9/2011 | Halle et al. |
| 2011/0301073 | A1 | 12/2011 | Gregory et al. |
| 2012/0110685 | A1 | 5/2012 | Bonas et al. |
| 2012/0178131 | A1 | 7/2012 | Voytas et al. |
| 2012/0178169 | A1 | 7/2012 | Voytas et al. |
| 2012/0192301 | A1 | 7/2012 | Jaenisch et al. |
| 2012/0214228 | A1 | 8/2012 | Voytas et al. |
| 2012/0222143 | A1 | 8/2012 | Fahrenkrug et al. |
| 2015/0167010 | A1 | 6/2015 | Lamb et al. |
| 2018/0023062 | A1 | 1/2018 | Lamb et al. |

FOREIGN PATENT DOCUMENTS

WO  WO 2001/066780  9/2001

OTHER PUBLICATIONS

Yu et al 2007 (PNAS 104:21 p. 8924-8929).*
Sheridan and Auger 2006 (Genetics 174: p. 1755-1765).*
U.S. Appl. No. 14/209,828, filed Mar. 13, 2014, Lamb et al.
U.S. Appl. No. 14/109,823, filed Dec. 14, 2013, Lamb et al.
Akopian et al., "Chimeric recombinases with designed DNA sequence recognition," *Proc Natl Acad Sci USA* 100(15):8688-91, 2003.
Baudat et al., "PRDM9 is a major determinant of meiotic recombination hotspots in humans and mice," *Science* 327(5967):836-40, 2010.
Boch et al., "Breaking the code of DNA binding specificity of TAL-type III effectors," *Science* 326:1509-1512, 2009.
Bogdanove et al., "TAL Effectors: Customizable Proteins for DNA Targeting," *Science* 333:1843-1846, 2011.
Broothaerts et al., "Gene transfer to plants by diverse species of bacteria," *Nature* 443(7026):629-633, 2005.
Bruce et al., "Influence of retinoblastoma-related gene silencing on the initiation of DNA replication by African cassava mosaic virus Rep in cells of mature leaves in Nicotiana benthamiana plants," *Virol J.* 8:561, 2011.
Buchholz et al., "In vitro evolution and analysis of HIV-1 LTR-specific recombinases," *Methods* 53(1):102-109, 2011.
Comeau et al., "Media for the in ovuloculture of proembryos of wheat and wheat-derived interspecific hybrids or haploids," *Plant Sci* 81(1):117-125, 1992.
Copenhaver et al., "Genetic definition and sequence analysis of Arabidopsis centromeres," *Science* 286(5449):2468-74, 1999.
Deng et al., "Structural Basis for Sequence-Specific Recognition of DNA by TAL Effectors," *Science* 335:720-723, 2012.
Dhar et al., "Architecture of the Hin Synaptic Complex during Recombination," *Cell* 119(1):33-45, 2004.
Gaj et al., "Structure-guided reprogramming of serine recombinase DNA sequence specificity," *Proc Natl Acad Sci USA* 108(2):498-503, 2011.
Garcia-Otin et al., "Mammalian genome targeting using site-specific recombinases," *Frontiers in Bioscience* 11:1108-1136, 2006.
Gelvin, "Agrobacterium-Mediated Plant Transformation: the Biology behind the 'Gene-Jockeying' Tool," *Microbiology and Molecular Biology Reviews* 67(1):16-37, 2003.
Gersbach et al., "Directed evolution of recombinase specificity by split gene reassembly," *Nucleic Acids Res* 38(12):4198-4206, 2010.
Gordley et al., "Evolution of programmable zinc finger-recombinases with activity in human cells," *J Mol Biol* 367(3):802-13, 2007.
Gordley et al., "Synthesis of programmable integrases," *Proc Natl Acad Sci USA* 106(13):5053-5058, 2009.
Grindley et al., "Mechanisms of site-specific recombination," *Annu Rev Biochem* 75:567-605, 2006.
Hellens et al., "Technical Focus: A guide to Agrobacterium binary Ti vectors," *Trends in Plant Science* 5(10):446-451, 2000.
Hughes et al., "Sequence-specific interaction of the Salmonella Hin recombinase in both major and minor grooves of DNA," *EMBO J.* 11(7):2695-2705, 1992.

(Continued)

*Primary Examiner* — Matthew R Keogh
(74) *Attorney, Agent, or Firm* — Dentons US LLP

(57) ABSTRACT

The current invention provides methods for creating a block of genetically linked transgenic traits or a megalocus that can be transmitted as a single genetic unit. The present invention further provides methods for trait introgression to other plants, varieties or species using the megaloci of the invention. Also provided are plants, seeds, and plant parts comprising the megaloci.

11 Claims, 3 Drawing Sheets

(56) References Cited

OTHER PUBLICATIONS

Iida et al., "A tale of two integrations, transgene and T-DNA: gene targeting by homologous recombination in rice," *Current Opinion in Biotechnology* 15(2):132-138, 2004.
Koo et al., "Distinct DNA methylation patterns associated with active and inactive centromeres of the maize B chromosome," *Genome Res.* 21(6):908-914, 2011.
Lamb et al., "A hemicentric inversion in the maize line knobless Tama flint created two sites of centromeric elements and moved the kinetochore-forming region," *Chromosoma* 116(3):237-47, 2007.
Mak et al., "The Crystal Structure of TAL Effector PthXo I Bound to Its DNA Target," *Science* 335:716-719, 2012.
Mercer et al., "Chimeric TALE recombinases with programmable DNA sequence specificity," *Nucleic Acids Res* 40(21):11163-72, 2012.
Miki et al., "Procedures for Introducing Foreign DNA into Plants," *Methods in Plant Molecular Biology and Biotechnology* 1993.
Miller et al., "A TALE nuclease architecture for efficient genome editing," *Nat Biotechnol* 29(2):143-8, 2011.
Mor et al., "Geminivirus vectors for high-level expression of foreign proteins in plant cells," *Biotechnol Bioeng.* 81(4):430-7, 2003.
Moscou et al., "A Simple Cipher Governs DNA Recognition by TAL Effectors," *Science* 326:1501, 2009.
Nagy, "Cre recombinase: The universal reagent for genome tailoring," *Genesis* 26(2):99-109, 2000.
Nern et al., "Multiple new site-specific recombinases for use in manipulating animal genomes," *Proc Natl Acad Sci USA* 108(34):14198-203, 2011.
Proudfoot et al., "Zinc finger recombinases with adaptable DNA sequence specificity," *PLoS One* 6(4):e19537, 2011.
Rimphanitchayakit et al., "Saturation mutagenesis of the DNA site bound by the small carboxy-terminal domain of gamma delta resolvase,"*EMBO J.* 9(3):719-725, 1990.
Schornack et al., "Gene-for-gene-mediated recognition of nuclear-targeted AvrBs3-like bacterial effector proteins," *J Plant Physiology* 163(3):256-272, 2006.
Smith et al., "Diversity in the serine recombinases," *Molecular Microbiology* 44(2):299-307, 2002.
Sun et al., "Optimized TAL effector nucleases (TALENs) for use in treatment of sickle cell disease," *Mol Biosyst* 8(4):1255-63, 2012.
Szurek et al., "Type III-dependent translocation of the Xanthomonas AvrBs3 protein into the plant cell," *Mol Microbiol* 46(1):13-23, 2002.
Torney et al., "Mesoporous silica nanoparticles deliver DNA and chemicals into plants," *Nature Nanotechnology* 2:295-300, 2007.
Turan et al., "Site-specific recombinases: from tag-and-target- to tag-and-exchange-based genomic modifications," *FASEB Journal* 25:4088-4107, 2011.
Tucker et al., "Riboswitches as versatile gene control elements," *Current Opinion in Structural Biology* 15(3):342-348, 2005.
Vergunst et al., "VirB/D4-Dependent Protein Translocation from Agrobacterium into Plant Cells," *Science* 290(5493):979-982, 2000.
Willment et al., "Identification of long intergenic region sequences involved in maize streak virus replication," *J Gen Virol.* 88(pt 6):1831-41, 2007.
You et al., "Use of Bacterial Quorum-Sensing Components to Regulate Gene Expression in Plants," *Plant Physiology* 140(4):1205-1212, 2006.
Zhu et al., "Cleavage-dependent ligation by the FLP recombinase. Characterization of a mutant FLP protein with an alteration in a catalytic amino acid," *J. Biol Chem* 270(30):23044-23054, 1995.
U.S. Appl. No. 15/633,591, filed Jun. 26, 2017, Lamb et al.
Birchler et al., "Recombination in the B chromosome of Maize to Produce A-B-A Chromosomes," *Genetics* 126:723-733, 1990.

* cited by examiner ns; (b) crossing the hybrid plant with itself or a distinct
CREATION AND TRANSMISSION OF MEGALOCI

CROSS REFERENCE TO RELATED APPLICATIONS

This application claims the benefit of U.S. Provisional Application No. 61/787,894, filed Mar. 15, 2013, herein incorporated by reference in its entirety.

FIELD OF THE INVENTION

The invention relates generally to the fields of molecular biology and genetics. More particularly, the invention relates to methods for the creation of stacks of transgenic loci that segregate together.

BACKGROUND OF THE INVENTION

To achieve desired traits or phenotypes in a plant, the introduction of more than one transgene may be needed. Methods of introducing multiple transgenes into a single plant are known in the art, although such methods are often complicated by recombination, which can separate desired loci. Methods are needed to enable reliable transmission of multiple loci as a single genetic entity.

BRIEF SUMMARY OF THE INVENTION

In one aspect, the invention provides a method for producing a megalocus on a plant chromosome comprising: (a) obtaining a hybrid plant comprising a first locus and a second locus, where the first locus is transgenic and the second locus comprises an endogenous trait locus or is transgenic, where the first and second loci are located on different homologous chromosomes, and where the loci are at genetically linked positions in said homologous chromosomes; (b) crossing the hybrid plant with itself or a distinct plant; and (c) selecting a progeny plant produced from step (b) wherein genetic recombination has occurred between said first locus and said second locus to produce a megalocus comprising the first and second loci arranged in cis. In one embodiment, the method further comprises (d) obtaining a further hybrid plant comprising said megalocus and a third locus, where the third locus is transgenic, where the megalocus and third locus are located on different homologous chromosomes, and wherein the megalocus and third locus are at genetically linked positions in said homologous chromosomes; (e) crossing the further hybrid plant with itself or a distinct plant; and (f) selecting a further progeny plant produced from step (e) wherein genetic recombination has occurred between said megalocus and said third locus to produce a further megalocus comprising the first, second and third loci arranged in cis. In another embodiment, steps (d)-(f) are repeated 2 or more times with still further hybrid plants comprising additional loci, where the additional loci are transgenic, to obtain yet a further megalocus comprising the first through third loci and the additional loci arranged in cis. In another embodiment, obtaining the hybrid plant comprises crossing a first plant comprising the first locus with a second plant comprising the second locus. In still another embodiment, the loci of the megalocus are genetically linked but physically separate. In other embodiments, the chromosome is a supernumerary chromosome such as a B chromosome or an artificially derived chromosome. In other embodiments, the artificially derived chromosome is a truncated chromosome or a de novo generated chromosome. In another embodiment, the method further comprises one or both of (i) transforming said first plant or a progenitor thereof with a transgene to produce said a first locus; or (ii) transforming said second plant or a progenitor thereof with a transgene to produce said a second locus; wherein said transforming occurs prior to step (a). In still other embodiments, the transforming comprises site-specific introduction of a transgene to produce the first locus at a position genetically linked with said second locus. In other embodiments, genetic recombination comprises meiotic recombination or induced recombination.

In embodiments of the invention, the loci of the megalocus are located about 0.1 cM to about 20 cM apart from each other; or the loci of the megalocus are located about 0.1, 0.2, 0.3, 0.4, 0.5, 0.6, 0.7, 0.8, 0.9, 1, 1.5, 2, 2.5, 3, 5, 10, 15 or 20 cM apart from each other; or neutral or favorable loci are located between the loci of the megalocus. In some embodiments, the progeny plant produced from step (b) is hemizygous or homozygous for said megalocus. In other embodiments, the megalocus is introgressed into a plant of the same variety as said first plant or a distinct variety from said first plant, and the introgression may comprise a haploid induction cross. In still further embodiments, the megalocus is introgressed into a plant of a distinct species from said first plant. In another embodiment, the invention provides a chromosome comprising the megalocus produced as described. In an embodiment, the chromosome is a supernumerary chromosome. In another embodiment, the supernumerary chromosome does not exhibit non-disjunction. In still a further embodiment, the invention provides a transgenic plant, seed or plant part comprising the megalocus produced as described.

In another aspect, the invention provides a method of producing a megalocus in a region of a chromosome lacking spontaneous meiotic recombination, comprising: (a) obtaining a hybrid plant comprising a first locus and a second locus, where the first locus is transgenic and the second locus comprises an endogenous trait locus or is transgenic, where the first and second loci are located on different homologous chromosomes, wherein the loci are located in a region of said homologous chromosomes lacking spontaneous meiotic recombination; (b) inducing genetic recombination to occur between said first and second loci; (c) crossing the hybrid plant with itself or a distinct plant; and (d) selecting a progeny plant comprising a megalocus comprising the first and second loci located in cis within said region. In an embodiment, the method further comprises: (e) obtaining a further hybrid plant comprising said megalocus and third locus, where the third locus is transgenic, where the megalocus and third locus are located on different homologous chromosomes and within said region lacking spontaneous meiotic recombination; (f) inducing genetic recombination to occur between said megalocus and third locus; (g) crossing the further hybrid plant with itself or a distinct plant; and (h) selecting a further progeny plant comprising a further megalocus comprising the first, second and third loci located in cis within said region. In another embodiment, steps (e) and (h) are repeated 2 or more times with still further hybrid plants comprising additional loci, where the additional loci are transgenic, to obtain yet a further megalocus comprising the first through third loci and the additional loci arranged in cis within said region. In other embodiments, the chromosome is a supernumerary chromosome or a nuclear chromosome. In another embodiment, the loci of the megalocus are genetically linked but physically separate. In another embodiment, the region lacks spontaneous meiotic recombination due to a chromosomal rearrangement such as an inversion or a translocation. In another embodiment, genetic recombination comprises induced meiotic recombination or chromosomal rearrangement. In other embodiments, the method further comprises one or both of: (i) transforming said first plant or a progenitor thereof with a transgene to produce said first locus; or (ii) transforming said second plant or a progenitor thereof with a transgene to produce said second locus; wherein said transforming occurs prior to step (a). In other embodiments, the transforming is site-specific or neutral or favorable loci are located between the loci of the megalocus. In other embodiments, the method further comprises introgressing the megalocus into a plant of a different variety or into a plant of a different species, or the introgressing may comprise a haploid induction cross. In another embodiment, the invention provides a chromosome comprising a megalocus produced by the method described herein, and a transgenic plant, seed, or plant part comprising a megalocus produced by the method described herein.

DETAILED DESCRIPTION OF THE INVENTION

Figure 1:
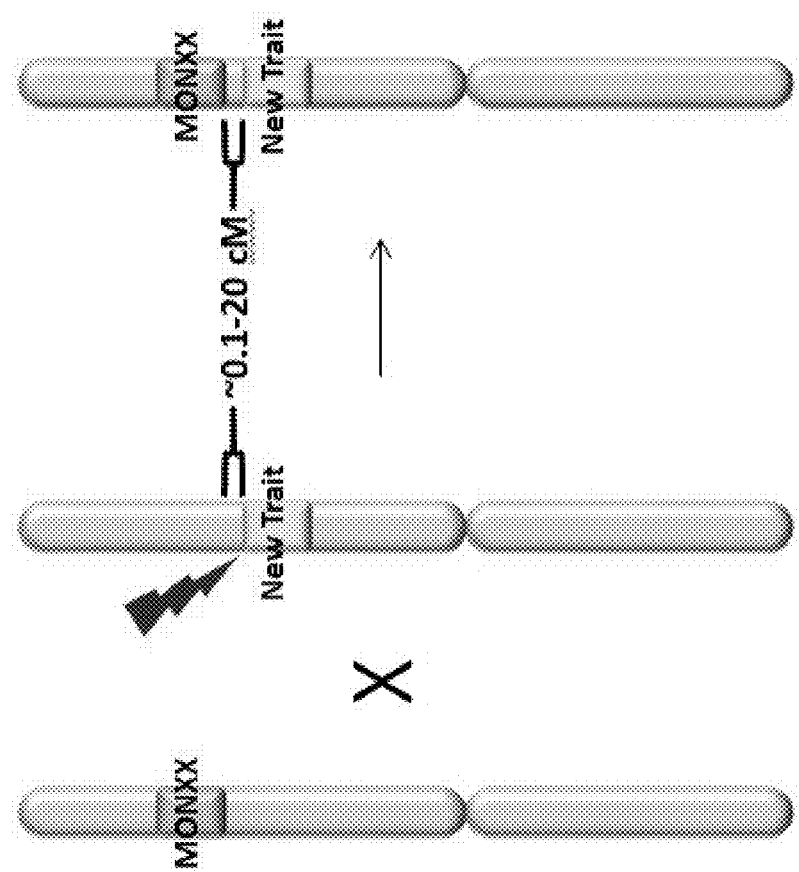
FIG. 1: Shows a diagram of site-directed integration to reduce genetic loci for trait introgression. MONXX denotes an existing transgenic event. Desired transgenes are placed within close genetic proximity to each other, or a desired transgene is placed within close proximity to a desired endogenous trait.

The present invention provides methods for creating blocks of genetically linked transgenic loci (i.e., a megalocus) that can be transmitted as a single genetic unit through a trait introgression process to other plants, varieties or species. In one embodiment, the invention provides methods for use of two or more transformants, created through targeted transformation of at least one transgene that produces a desirable trait in a plant, followed by recombination linking the desired transgenes to form a megalocus.

Such an approach of targeted transformation followed by recombination to link desired transgenes possesses advantages of both vector stacks and breeding stacks without many of the limitations. For example, in one embodiment, individual transgenes may be introduced one at a time and combined at a later date. In another embodiment, the insertion sites of the individual desired transgenes may be genetically linked but physically separate relative to a second transgene insertion site, i.e., an "event", or a set of transgene insertion sites/events. In another embodiment, individual desired transgenes may be physically separated by a distance of between about 0.1 cM to about 20 cM, including 0.1, 0.2, 0.3, 0.4, 0.5, 0.6, 0.7, 0.8, 0.9, 1, 1.5, 2, 2.5, 3, 5, 10, 15, and 20 cM.

In a further embodiment of the invention, the insertion site of individual desired transgenes may not be genetically linked, or may not be closely linked, such as at least about 10, 20, 30, 40 or more cM apart. Once transgenes are combined in cis on the same chromosome, they could be induced to be genetically linked by chromosome rearrangement of the intervening sequences, thus allowing numerous independent transgenes to be easily introgressed into different germplasm. In a further embodiment, two plant lines, each containing different transgenes that have been combined to form a megalocus at a linked site in trans, can be crossed together to create one large megalocus in cis, containing all of the transgenes.

Linking transgenic traits together as a genetic linkage block may be desirable due to the ability to reduce the number of randomly segregating transgenic loci in the trait integration process. Stacking of transgenes that are genetically linked may also reduce the number of progeny to be screened to find stacked transgenes during the trait integration process. Additionally, combining site-directed integration and utilizing the endogenous meiotic recombination machinery to link transgenes provides extra flexibility in product concepts that speeds up product delivery timelines. A further embodiment of the invention is the combination of site-directed integration with technology to modify meiotic recombination machinery wherein such technology includes transgenic modification of gene expression or chemical treatments to modulate recombination.

Genetically linking traits by recombination effectively reduces trait loci for trait introgression while still providing flexibility. For instance, by employing methods of the present invention, several transgenes conferring the same or different traits may be tested at the same loci, rather than vector stacking the traits, allowing testing of several combinations of traits and versions of traits simultaneously before deciding on a commercial product. With vector stacking, it is necessary to make decisions regarding commercial product concepts several years in advance, which reduces flexibility. In accordance with some embodiments of the present invention, a next-generation trait may be tested at the same locus or nearby locus as a previous trait, which may then replace the previous trait by recombining out the previous trait and recombining in the next-generation trait. This invention also anticipates inclusion of target recognition sites within gene expression cassettes to enable insertion and deletion of transgenes and transgenic elements within at least one gene expression cassette.

Methods of creating transgenic events currently found in the art typically utilize nuclear chromosomes for insertion of transgenes. Such nuclear chromosomes are generally susceptible to spontaneous meiotic recombination. In one embodiment, the present invention provides an advantage over currently available technology by utilizing plant B chromosomes as a location for creation of a megalocus. Placing a transgene or megalocus of transgenes onto a B chromosome has additional advantages compared to a transgene or megalocus of transgenes on a normal or A chromosome. Such an approach may allow for transgenic events containing one or more transgenes to be created and tested independently. After the desired events are selected, they may then be combined with other desired events into a single genetic entity that is easily introgressed into different plant varieties via backcrossing. Because events according to the present invention may be on an entity (e.g., a B chromosome) that is distinct from the rest of the genome, the introgression process does not need to "clean up" events (remove genetic information/marker near the event) by identifying recombination events that are close to the event. In addition, a B chromosome and any transgenes it carries will transmit as a diploid in complex polyploids, thus simplifying complicated genetics of species such as sugarcane.

In another embodiment, the present invention provides an advantage over currently available technology by introducing the desired transgenes in chromosomal regions that lack spontaneous recombination. Such regions may naturally lack spontaneous recombination or may be induced to lack spontaneous recombination by any of the number of methods known in the art. For instance, the desired transgenes may be introduced into a chromosome at sites that are independent of each other but remain tightly genetically linked, such as centromeric regions, which comprise millions of base pairs and contain many genes but demonstrate no meiotic recombination. In other embodiments, sites that are not closely genetically linked may be made to lack recombination through methods to block spontaneous recombination, such as chromosomal rearrangements, or chemical or transgenic suppression of recombination.

In further embodiment of the invention, the initial transformants may be crossed to each other to produce hybrid progeny containing the desired transgenes from both parents. The hybrid may then be selfed or outcrossed to allow recombination to occur, and the progeny screened for individuals containing all of the desired transgenes on a single chromosome in cis. A hybrid may be selfed for one or more generations, which may include 1, 2, 3, 4, 5, 6, 7, 8, 9, 10, or more generations. Because such a recombination containing all of the desired transgenes may be rare, any number of progeny may be screened to identify those comprising all desired transgenes.

As used herein, a "megalocus" refers to a block of genetically linked transgenic traits that are normally inherited as a single unit. A megalocus according to the invention may provide to a plant one or more desired traits, which may include, but are not limited to, enhanced growth, drought tolerance, salt tolerance, herbicide tolerance, insect resistance, pest resistance, disease resistance, and the like. In specific embodiments, a megalocus comprises at least about 2, 3, 4, 5, 6, 7, 8, 9, 10, 11, 13 or 15 transgenic loci (events) that are physically separated but genetically linked such that they can are inherited as a single unit. Each transgenic locus in the megalocus can be 0.1, 0.2, 0.3, 0.4, 0.5, 0.6, 0.7, 0.8, 0.9, 1, 1.5, 2, 2.5, 3, 5, 10, 15, or 20 cM apart from one another.

Supernumerary Chromosomes

Extra, dispensable chromosomes are present in many species, including several species used for agricultural purposes, such as corn and rye. These supernumerary chromosomes are often referred to as "B" chromosomes, while the normal genetic complement is referred to as the "A" genome or "A" chromosomes. When two B chromosomes are present in a single plant, the two B chromosomes will pair with each other at meiotic prophase and recombination can occur. B chromosomes do not pair with or recombine with the other chromosomes.

In one embodiment, methods of the present invention incorporate desired transgenes into a supernumerary chromosome. A supernumerary chromosome may be, for example, a naturally occurring chromosome such as a plant B chromosome. In another embodiment, a supernumerary chromosome may be an artificially derived chromosome, such as a truncated chromosome or a de novo generated chromosome.

A B chromosome according to certain embodiments of the present invention may be delivered to a progeny plant without the rest of the genome (e.g., via a haploid induction cross that retains the B chromosome), allowing complete conversion to a new variety in a single cross. In other embodiments, a B chromosome may be transferred to other species, allowing testing of the transgene or transgenes in other crops. For example, transmission of a B chromosome to oat has been demonstrated, as well as transmission of a corn chromosome to wheat (Koo et al., *Genome Res* 21(6): 908-914, 2011; Comeau et al., *Plant Sci* 81(1):117-125, 1992).

In certain cases, such as in corn and rye, B chromosomes have "accumulation mechanisms" that allow them to transmit at greater than Mendelian frequencies. For example, in corn, the sister chromatids of the B chromosome fail to separate during the second pollen (first generative) division. As a result, both sister chromatids are delivered to one of the sperm, while the other receives neither. This effect, called non-disjunction, means that a plant with only a single B chromosome can deliver two B chromosomes to the next generation when used as a male. Such an effect may be desirable during the trait introgression process, since it allows individuals that are homozygous (as opposed to hemizygous) for the megalocus carried on a B chromosome to be recovered in a backcross, as long as the B chromosome is delivered from the pollen.

The non-disjunction effect requires that specific portions of the B chromosome be present. A trans-acting piece at the tip of the long arm and a cis-acting piece near the centromere are required. Very small deletions at the tip of the long arm of the B chromosome are recoverable and the resulting B chromosomes do not exhibit non-disjunction. In certain embodiments of the invention, such a deletion variant of the B chromosome may be desired, for instance, for the purpose of delivering a megalocus for commercial traits.

In certain embodiments of the invention, methods can be employed to cause programmed loss of the transgenic chromosome. One such method is to flank the B chromosome centromere with recombination sites (e.g. LoxP sites). Alternately, recombination sites may flank an entire megalocus. A recombinase expressed in the male flowers of the hybrid plants may then be grown in the field. The recombinase would remove the megalocus or the B chromosome centromere, thus preventing transmission of the megalocus.

Chromosome Regions Lacking Spontaneous Meiotic Recombination

One embodiment of the present invention provides building a megalocus that may be useful for trait introgression at a region lacking spontaneous meiotic recombination. Events may be placed at sites that are far enough apart that they are independent of each other but that are completely linked genetically. It is known in the art that recombination frequency is not evenly distributed along chromosomes. For example, centromeric regions are comprised of millions of base pairs and contain many genes; however, there is no meiotic recombination in those regions. Events placed at sites within such a recombination-free region will be completely linked and therefore be transmitted through a trait introgression program in the same manner as a single event.

In one embodiment the invention provides methods for building a megalocus wherein the several traits involved may be simultaneously introduced or introduced through serial transformation events to sites on the same chromosome in such regions. In another embodiment, the transgenic events may be created in different lines and later incorporated as into a single individual by crossing. Progeny may then be recovered containing a chromosome with the desired transgenes on a single chromosome. Even though spontaneous meiotic recombination would not occur between the sites, mechanisms exist that can cause the desired chromosome rearrangement. Such mechanisms are known in the art and include, but are not limited to, induced recombination at meiosis with the use of a nuclease, and chromosomal rearrangement induced by nuclease or recombinase activity or by DNA damaging agents.

In certain embodiments, such recombination may be induced by a cut at a location between two sites, either in meiosis or in mitosis preceding meiosis, in one or both chromosomes containing desired events. The resulting chromosome, comprising the previously separate events, may then be delivered to an offspring. Similarly, a recombinase such as a transcription activator-like effector (TALE) recombinase (TALER) may be used to cause the necessary chromosomal rearrangement between the two chromosomes containing the desired transgenes.

DNA damaging agents can also cause chromosomal rearrangements that may result in a megalocus according to the present invention. Such agents may include, but are not limited to UV or X-rays, as well as any other known DNA damaging agents.

Chemical or environmental treatments that alter the meiotic recombination profile also produce recombination useful in the present invention. For example, several chemical treatments have been shown to increase the genetic distance around centromeres in *Arabidopsis* (Copenhaver et al., *Science* 286(5449): 2468-74, 1999), including methanesulfonic acid ethyl ester (0.05%), 5-aza-2'-deoxycytidine (25 or 100 mg/L), Zeocin (1 µg/ml), methanesulfonic acid methyl ester (75 parts per million), cis-diamminedichloroplatinum (20 µg/ml), mitomycin C (10 mg/L), N-nitroso-N-ethylurea (100 µM), n-butyric acid (20 µM), trichostatin A (10 µM), or 3-methoxybenzamide (2 mM).

Recombination hotspots and coldspots have been identified in many species, including corn, and the position of hotspots and coldspots can vary among different individuals.

By identifying and taking advantage of such hotspots and coldspots, a megalocus according to the present invention may be designed in a region that is not recombined, or is recombined at a low level, in one variety, but is recombined in another variety or in a hybrid with another variety. In such a situation, formation of a megalocus from separately transformed traits may be accomplished in one variety and trait introgression may be performed in another variety.

Alternatively, hotspots and coldspots can be altered by expression of engineered hotspot-inducing or -repressing proteins. Proteins with engineered DNA binding domains (e.g., TALEs or zinc fingers) fused to such hotspot-inducing or -repressing proteins could be used to modulate recombination rates. One such example of a hotspot inducing protein is the PRDM9 protein, which trimethylates H3K4 (Baudat et al., *Science*, 327(5967):836-40, 2010). Targeting the histone methyltransferase domain of PRDM9 or other such chromatin remodeling domains to specific loci may cause hotspot formation at desired locations, thus increasing recombination rates or causing recombination at regions that were previously recombination free.

Alternatively, identification of DNA sequence binding sites for endogenous plant hotspot-inducing proteins may allow such sites to be added to transgenes placed in regions of no recombination, thus allowing the subsequent linkage of traits by meiotic recombination. Alternatively, altering DNA sequence binding sites for hotspot-inducing proteins may alter the recombination rate that that site.

A line expressing a gene that may help with assembly of a megalocus, for example a hotspot-inducing gene or a recombinase (e.g. TALER) engineered to affect the region between two sites in an otherwise recombination-free zone, may be crossed with the traits to be linked in order to assemble a megalocus. Subsequently, the helper gene may be crossed out so that the two traits would remain completely linked during the trait introgression process.

Methods described herein for linking traits added to sites in a recombination-free region would also function for linking genes in a region that does experience recombination. In such a case, these methods may be used to facilitate megalocus assembly as an alternative to meiotic recombination, or to increase the efficiency of recovering the desired recombined chromosome by meiotic recombination.

Elimination or Reduction of Recombination

Chromosome rearrangements may also affect recombination rates. This type of rearrangement may be undetected between lines and exhibit no deleterious phenotype. However, one result of such a rearrangement may be that the genetic distance may be very low or even zero at a location in one line, while higher in another line. A third rate of recombination may exist for this region between chromosomes in a hybrid of the two lines.

Classic studies of chromosome rearrangements showed that recombination is typically reduced or repressed between regions of two chromosomes that are rearranged relative to one another. Inversions in a chromosome can block recombination between the inverted region and the corresponding region of the non-inverted chromosome. For example, a large region of chromosome 8 was found to be inverted in the knobless Tama flint corn line (KTF) (Lamb et al., *Chromosoma* 116(3):237-47, 2007). This inversion resulted in blockage of recombination of the region between and around the inversion breakpoints.

Non-recombining segments at desired locations can be created by using TALERs or nucleases to cause chromosome rearrangements. Inversions within inversions are preferred when large genetic and/or physical distances are desired to be included in the non-recombining segment. Translocation can also be used where the breakpoint of one translocation is in or near the region where the non-recombining segment is desired. Many corn lines with rearrangements are available from public repositories. Similar collections are also available for other plants. In the case of corn, many lines with chromosomal rearrangements were derived from seeds exposed to nuclear radiation and the collection of corn lines with rearrangements could be expanded by exposing plants to DNA damaging treatments such as X-rays.

Transgene Expression Constructs

The construction of vectors which may be employed in conjunction with plant transformation techniques using desired transgenes according to the invention are known to those of skill of the art in light of the present disclosure (see, for example, Sambrook et al., In: Molecular cloning, Cold Spring Harbor Laboratory Press, Cold Spring Harbor, N.Y., 2001; Gelvin et al., In: Plant Molecular Biology Manual, 1990). Use of the various embodiments of the current invention are not limited to any particular nucleic acid sequences.

DNA segments used for transforming plant cells generally comprise RNA coding sequence, cDNA, gene, or genes which one desires to introduce into and have expressed in the host cells. These DNA segments can further include structures such as promoters, enhancers, polylinkers, regulatory genes, and/or any other sequence, as desired. The DNA segment or gene chosen for cellular introduction may encode a protein which will be expressed in the resultant recombinant cells, resulting in a screenable or selectable trait and/or which will impart an improved phenotype to the resulting transgenic plant. However, this may not always be the case, and various embodiments of the present invention also encompass transgenic plants incorporating non-expressed transgenes. Components likely to be included with vectors used in the current invention are listed in the following for exemplary purposes only and are not limited to those listed.

Regulatory Elements

Promoters for expression of a transgene are known in the art and, in certain aspects, a promoter for use according to the invention may be any promoter known to drive expression in the desired individual, such as a plant. Promoters for use in accordance with the present invention therefore may include, but are not limited to, plant promoters such as the CaMV 35S promoter (Odell et al., *Nature*, 313:810-812, 1985), or others such as CaMV 19S (Lawton et al., *Plant Mol. Biol.* 9:315-324, 1987), nos (Ebert et al., *Proc. Nat'l Acad. Sci. USA*, 84:5745-5749, 1987), Adh (Walker et al., *Proc. Natl. Acad. Sci. USA*, 84:6624-6628, 1987), sucrose synthase (Yang and Russell, *Proc. Natl. Acad. Sci. USA*, 87:4144-4148, 1990), α-tubulin, actin (Wang et al., *Molecular and Cellular Biology*, 12(8):3399-3406, 1992), cab (Sullivan, et al., *Mol. Gen. Genet.*, 215(3):431-440, 1989), PEPCase (Hudspeth and Grula, *Plant Mol. Biol.*, 12:579-589, 1989) or those associated with the R gene complex (Chandler et al., *The Plant Cell*, 1:1175-1183, 1989). Tissue-specific promoters such as root cell promoters (Conkling et al., *Plant Physiol.*, 93:1203-1211, 1990) and tissue-specific enhancers (Fromm et al., *Nature* 319:791-793, 1986) may also be useful, as are inducible promoters such as ABA- and turgor-inducible promoters.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure.

It is specifically envisioned that transgene coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an α or β-tubulin gene that also directs expression in roots.

Terminators

Transformation constructs prepared in accordance with the invention will typically include a 3' end DNA sequence that acts as a signal to terminate transcription and allow for the poly-adenylation of the mRNA produced by coding sequences operably linked to a transgene. Terminators which may be useful for this invention include those from the nopaline synthase gene of *Agrobacterium tumefaciens* (nos 3' end) (Bevan et al., *Nucleic Acids Research*, 11(2):369-385, 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., *Genes Dev.*, 1:1183-1200, 1987), sucrose synthase intron (Vasil et al., *Plant Physiol.*, 91:1575-1579, 1989) or TMV omega element (Gallie et al., *The Plant Cell*, 1:301-311, 1989), may further be included where desired.

Intron Sequences

In certain aspects, intron sequences are included in a gene expression cassette and may enhance transgene expression. In certain aspects, an intron in accordance with the present invention include any intron known in the art, including but not limited to a Ract1, TubA, Sus1, or Hsp70 intron.

Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids, and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It is further contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

Marker Genes

By employing a selectable or screenable marker protein, one can provide or enhance the ability to identify transformants. "Marker genes" are genes that impart a distinct phenotype to cells expressing the marker protein and often provide a means to more efficiently distinguish such transformed cells from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable markers" also are genes which encode a "secretable marker"

whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., *Mol. Gen. Genet.*, 199:183-188, 1985), which provides kanamycin resistance and can be selected for using kanamycin, G418, paromomycin, etc.; bar, which confers bialaphos or phosphinothricin resistance; a mutant EPSP synthase protein (Hinchee et al., *Bio/technol.*, 6:915-922, 1988) conferring glyphosate resistance; a nitrilase such as bxn from *Klebsiella ozaenae* which confers resistance to bromoxynil (Stalker et al., *Science*, 242:419-422, 1988); a mutant acetolactate synthase (ALS) which confers resistance to imidazolinone, sulfonylurea, or other ALS inhibiting chemicals (European Patent No. EP154204, 1985); a methotrexate resistant DHFR (Thillet et al., *J. Biol. Chem.*, 263:12500-12508, 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., In: Chromosome Structure and Function: Impact of New Concepts, 18th Stadler Genetics Symposium, 11:263-282, 1988); a β-lactamase gene (Sutcliffe, *Proc. Natl. Acad. Sci. USA*, 75:3737-3741, 1978), which encodes an enzyme for which various chromogenic substrates are known (e.g., PADAC, a chromogenic cephalosporin); a xylE gene (Zukowsky et al., *Proc. Natl. Acad. Sci. USA*, 80:1101-1105, 1983) which encodes a catechol dioxygenase that can convert chromogenic catechols; an α-amylase gene (Ikuta et al, *Bio/technol.*, 8:241-242, 1990); a tyrosinase gene (Katz et al., *J. Gen. Microbiol.*, 129:2703-2714, 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al, *Science*, 234:856-859, 1986), which allows for bioluminescence detection; an aequorin gene (Prasher et al., *Biochem. Biophys. Res. Commun.*, 126(3):1259-1268, 1985) which may be employed in calcium-sensitive bioluminescence detection; or a gene encoding for green fluorescent protein (Sheen et al., *Plant Journal*, 8(5):777-784, 1995; Haseloff et al., *Proc. Natl. Acad. Sci. USA*, 94(6):2122-2127, 1997; Reichel et al., *Proc. Natl. Acad. Sci. USA*, 93(12):5888-5893, 1996; Tian et al., *Plant Cell Rep.*, 16:267-271, 1997; WO 97/41228).

Example Transgenes

Male Sterility

Examples of genes conferring male sterility include those disclosed in U.S. Pat. Nos. 3,861,709; 3,710,511; 4,654,465; 5,625,132; and 4,727,219, each of the disclosures of which are specifically incorporated herein by reference in their entirety. The use of herbicide-inducible male sterility genes is described in U.S. Pat. No. 6,762,344. Induced male sterility in transgenic plants can increase the efficiency of hybrid seed production by eliminating the need to physically emasculate plants used as a female in a given cross.

Herbicide Tolerance

Numerous herbicide resistance genes are known and may be employed with the invention. An example is a gene conferring resistance to an herbicide that inhibits the growing point or meristem, such as an imidazalinone or a sulfonylurea. Exemplary genes in this category code for mutant ALS and AHAS enzyme as described, for example, by Lee et al., *EMBO J.*, 7:1241, 1988; Gleen et al., *Plant Molec. Biology*, 18:1185-1187, 1992; and Miki et al., *Theor. Appl. Genet.*, 80:449, 1990.

Resistance genes for glyphosate (resistance conferred by mutant 5-enolpyruvl-3 phosphikimate synthase (EPSPS) and aroA genes, respectively) and other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835 to Shah, et al., which discloses the nucleotide sequence of a form of EPSPS which can confer glyphosate resistance. Examples of specific EPSPS transformation events conferring glyphosate resistance are provided by U.S. Pat. No. 6,040,497.

Disease and Pest Resistance

Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al., *Science*, 266:7891, 1994 (cloning of the tomato Cf-9 gene for resistance to *Cladosporium fulvum*); Martin et al., *Science*, 262: 1432, 1993 (tomato Pto gene for resistance to *Pseudomonas syringae* pv.); and Mindrinos et al., *Cell*, 78(6):1089-1099, 1994 (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses (see Beachy et al., *Ann. Rev. Phytopathol.*, 28:451, 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus.

Insect Resistance

One example of an insect resistance gene includes a *Bacillus thuringiensis* protein, a derivative thereof, or a synthetic polypeptide modeled thereon. See, for example, Geiser et al., *Int. J. Health Serv.*, 16(1):105-120, 1986, who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example of insect resistance gene which could be used for the present invention is a lectin. See, for example, Van Damme et al., *Plant Molec. Biol.*, 24:25, 1994, who disclose the nucleotide sequences of several *Clivia miniata* mannose-binding lectin genes. A vitamin-binding protein may also be used, such as avidin (see PCT application US93/06487, the contents of which are hereby incorporated by reference). This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., *J. Biol. Chem.*, 262:16793, 1987 (nucleotide sequence of rice cysteine proteinase inhibitor), Huub et al., *Plant Molec. Biol.*, 21:985, 1993 (nucleotide sequence of cDNA encoding tobacco proteinase inhibitor I), and Sumitani et al., *Biosci. Biotech. Biochem.*, 57:1243, 1993 (nucleotide sequence of *Streptomyces nitrosporeus* α-amylase inhibitor). An insect-specific hormone or pheromone may also be used. See, for example, the disclosure by Hammock et al., *Nature*, 344:458, 1990, of baculovirus expression of cloned juvenile hormone esterase, an inactivator of juvenile hormone.

Antisense and RNAi Constructs

Antisense and RNAi sequences are known in the art. A transgene for use according to the invention may also comprise any antisense or RNAi coding sequence known in the art.

Plant Transformation and Breeding

Methods for transformation of plants are known in the art. Suitable methods of transforming plant cells include microinjection (Crossway et al. (1986) *Biotechniques* 4:320-334), electroporation (Riggs et al. (1986) *Proc. Natl. Acad. Sci. USA*, 83:5602-5606), *Agrobacterium* mediated transformation (Hinchee et al. (1988) *Biotechnology*, 6:915-921), direct gene transfer (Paszkowski et al. (1984) *EMBO J.*, 3:2717-2722), and ballistic particle acceleration (see, for example, Sanford et al., U.S. Pat. No. 4,945,050; WO 91/10725 and McCabe et al. (1988) Biotechnology, 6:923-926); all of which are herein incorporated by reference.

After effecting delivery of exogenous DNA to recipient cells via transformation, the next steps concern identifying the transformed cells for further culturing and plant regeneration. In order to improve the ability to identify transformants, one may desire to employ a selectable or screenable marker gene with a transformation vector prepared in accordance with the invention. In this case, one would then assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants.

To confirm the presence of the exogenous DNA or "transgene(s)" in the regenerating plants, mature plants, plant tissue and plant seeds, a variety of assays may be performed. Such assays include, for example, molecular biological assays, such as Southern and northern blotting and PCR; biochemical assays, such as detecting the presence of a protein product, e.g., by immunological means (ELISA and western blotting), or by enzymatic function; plant part assays, such as leaf or root assay; and also, by analyzing the phenotype of the whole regenerated plant.

These regenerated plants may then be pollinated with either the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

As used herein "cis" or "in cis" refers to different transgenes or genetic elements being present on the same strand of DNA. In the absence of recombination between two transgenes or genetic elements, genetic elements in cis are inherited together.

As used herein, an "event" refers to a transgenic event, in which a transgene is introduced or delivered to an organism. As used herein, "transgene" refers to a segment of DNA which has been incorporated into a host genome or is capable of autonomous replication in a host cell and is capable of causing the expression of one or more RNAs and/or polypeptides. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

As used herein, "DNA fragment" refers to any molecule of DNA, including but not limited to a protein-coding sequence, reporter gene, promoter, enhancer, intron, exon, poly-A tail, multiple cloning site, nuclear localization signal, or mRNA stabilization signal, or any other naturally occurring or synthetic DNA molecule. Alternatively, a DNA fragment may be completely of synthetic origin, produced in vitro. Furthermore, a DNA fragment may comprise any combination of isolated naturally occurring and/or synthetic fragments.

As used herein, "expression" refers to the combination of intracellular processes, including transcription. In the case of a functional RNA sequence, such as an antisense RNA, siRNA, or microRNA, expression may involve transcription and processing of the functional RNA. In the case of a polypeptide, coding sequence expression includes transcription and translation to produce a polypeptide.

As used herein, "gene expression cassette" refers to one or more transgenes operably linked to nucleic acid sequences that control expression of the transgene in a cell. The term gene expression cassette, expression cassette, and cassette are used interchangeably.

As used herein, "gene expression element" refers to expression control sequences that include but are not limited to promoters, enhancers, introns, terminators, and internal ribosome entry sites. Gene expression elements are combined with one or more genes of interest, or transgenes, into a gene expression cassette and govern the expression of the one or more transgenes in a desired way.

As used herein, "genetic transformation" refers to a process of introducing a DNA sequence or construct (e.g., a vector or gene expression cassette) into a cell or protoplast in which a heterologous DNA is incorporated into a chromosome.

As used herein, a "desired trait" or "trait of interest" or "gene of interest (GOI)" or "desired transgene" refers to the transgene conferring the desired phenotype, e.g., herbicide or insect resistance. The trait, transgene or GOI is part of the gene expression cassette.

As used herein "heterologous" refers to a sequence which is not normally present in a given host genome in the genetic context in which the sequence is currently found. In this respect, the sequence may be native to the host genome, but rearranged with respect to other genetic sequences within the host sequence. For example, a regulatory sequence may be heterologous in that it is linked to a different coding sequence relative to the native regulatory sequence. Furthermore, sequences and DNA molecules of the present invention may be heterologous to the organism, plant or cell they are comprised in.

As used herein, "isolating" refers to any process that allows the release of a DNA fragment from a larger DNA fragment. For example, a gene expression cassette can be isolated from a larger DNA fragment, e.g., a vector, by cutting the vector with restriction enzymes that flank the gene expression cassette. Often, the isolated DNA fragment is subsequently purified.

As used herein, "operably linked" refers to sub-elements that function together in a unit, e.g., the linkage of regulatory elements such as a promoter DNA molecule, a transit peptide encoding DNA molecule, and a polyadenylation signal-encoding DNA molecule linked to transcribable DNA in a manner that the transcribable DNA is readily transcribed, translated, and functionally localized in a transgenic plant cell. In certain embodiments, such operably linked elements may be heterologous with respect to each other.

As used herein, "selected DNA" refers to a DNA segment which one desires to use for a particular purpose.

As used herein, "stack" and "stacking" refers to a piece of DNA, such as a vector or chromosome comprising at least two gene expression cassettes. The cassettes are stacked in a vector or chromosome or other piece of DNA useful according to the invention. The process of combining at least two gene expression cassettes into one vector or chromosome is called stacking.

As used herein, "transcribable DNA" refers to a DNA molecule capable of being transcribed into an RNA molecule including, but not limited to, RNA that is translatable to a protein or polypeptide and RNA that is useful for gene suppression.

As used herein, "transformation construct" refers to a chimeric DNA molecule which is designed for introduction into a host genome by genetic transformation. Preferred transformation constructs will comprise all of the genetic elements necessary to direct the expression of one or more heterologous genes. In particular embodiments of the instant invention, it may be desirable to introduce a transformation construct into a host cell in the form of a gene expression cassette.

As used herein, "transformed cell" refers to a cell in which the DNA has been altered by the introduction of one or more heterologous DNA molecules into that cell.

As used herein, "transgenic plant" refers to a plant or progeny plant of any subsequent generation derived therefrom, wherein the DNA of the plant or progeny thereof contains an introduced heterologous DNA segment not naturally present at that location in a non-transgenic plant of the same variety. The transgenic plant may additionally contain sequences which are native to the plant being transformed, but wherein the gene has been altered in order to alter the level or pattern of expression of the gene, for example, by use of one or more heterologous regulatory or other elements.

As used herein, "a" or "an" may mean one or more. As used herein in the claim(s), when used in conjunction with the word "comprising," the words "a" or "an" may mean one or more than one.

As used herein the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The references cited herein, to the extent that they provide exemplary procedural or other details supplementary to those set forth herein, are specifically incorporated herein by reference.

EXAMPLES

The following examples provide illustrative embodiments of the invention. However, those of skill in the art should, in light of the present disclosure, appreciate that many changes can be made in specific aspects of these embodiments without departing from the concept, spirit, and scope of the invention. Moreover, it is apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

Example 1

Targeted Integration of a Desired Transgene into a Chromosome

At least one transgene will be targeted for integration into the genome at a specific locus that is genetically linked at a distance to another transgene that was either integrated randomly or through site-directed integration (FIG. 1). Individual transgenes to be combined in a megalocus will be produced on individual supernumerary chromosomes or in regions of nuclear chromosomes. A desired transgene may be targeted using site-directed integration technologies that are well known in the art. Such methodologies may include insertion by endonucleases (e.g. TALE nucleases, meganucleases, CRISPRs, zinc finger nucleases), recombinases (e.g. TALE-recombinases, zinc finger recombinases, Cre/lox, FLP/FRT), programmed group II introns, zinc finger or TALE chimeric transposases, and homology arm-mediated gene targeting, optionally employing a plus/minus selection scheme. Other methodologies that are useful to place traits at specific locations in the genome may be employed by the present invention.

Targeted transgenes will be placed on a chromosome within close genetic proximity to each other. For example, spacing desired transgenes 0.1 to 20 cM apart will allow for recombination between product/events, while still allowing trait introgression to breed as a single linkage block.

Example 2

Crossing Plants Harboring Desired Transgenes and Screening of Progeny

Plants harboring different desired transgenes will be crossed to each other to produce hybrid progeny with transgenes from both parents. Recombination in the progeny plants may occur spontaneously (e.g. during meiosis) or may be induced by either site-specific recombinases, nucleases, or the like, including chemical or transgenic modulators of recombination, to generate progeny with chromosomes containing transgenes from both parents. Alternately, during meiosis of the hybrid, supernumerary chromosomes will pair and a meiotic exchange can occur between the two events.

Progeny will be screened for recombinant plants that have the transgenes from both parents in cis on a single chromosome. The transgenes will thus be genetically linked and segregate as a linkage block for trait integration.

A resulting plant containing a supernumerary chromosome harboring all transgenes from both parents can be crossed to lines lacking supernumerary chromosomes or containing supernumerary chromosomes with which it is unable to pair. As long as the plant is not crossed with another plant containing a supernumerary chromosome with which it can pair, there will be no recombination that can separate the transgenes and thus the transgenes will transmit together as a single genetic unit.

Similarly, a resulting plant containing a nuclear chromosome harboring all transgenes from both parents in a region lacking spontaneous recombination can be crossed to lines containing chromosomes with which pairing is possible, but recombination does not spontaneously occur. As long as the transgenes are located in regions in which no spontaneous meiotic recombination will occur, the transgenes will not be separated and thus will transmit together as a single genetic unit.

Example 3

Addition of Multiple Desired Transgenes by Meiotic Recombination

Figure 2:
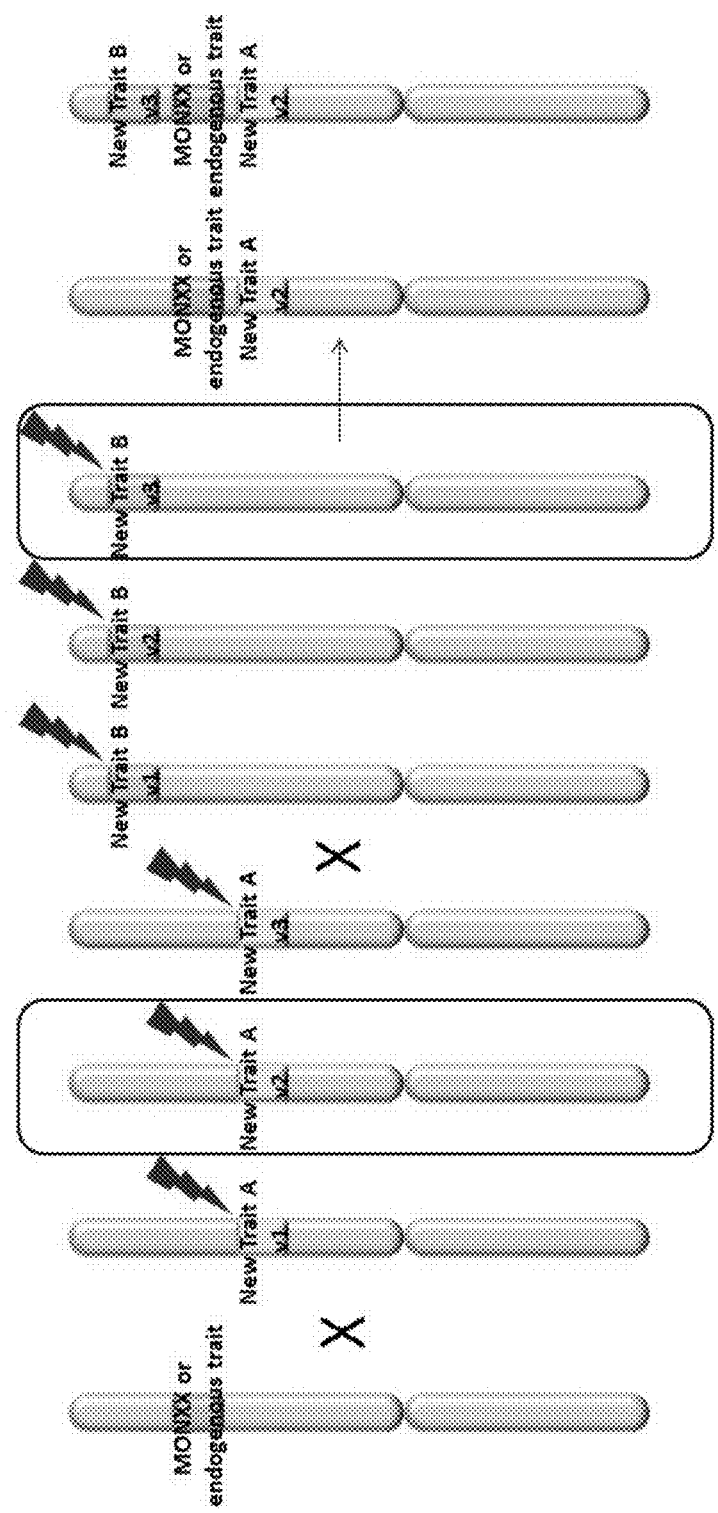
FIG. 2: Shows a schematic of a megalocus created from multiple recombination events with appropriate spacing between individual traits to allow flexibility for subsequent trait introgression.
Figure 3:
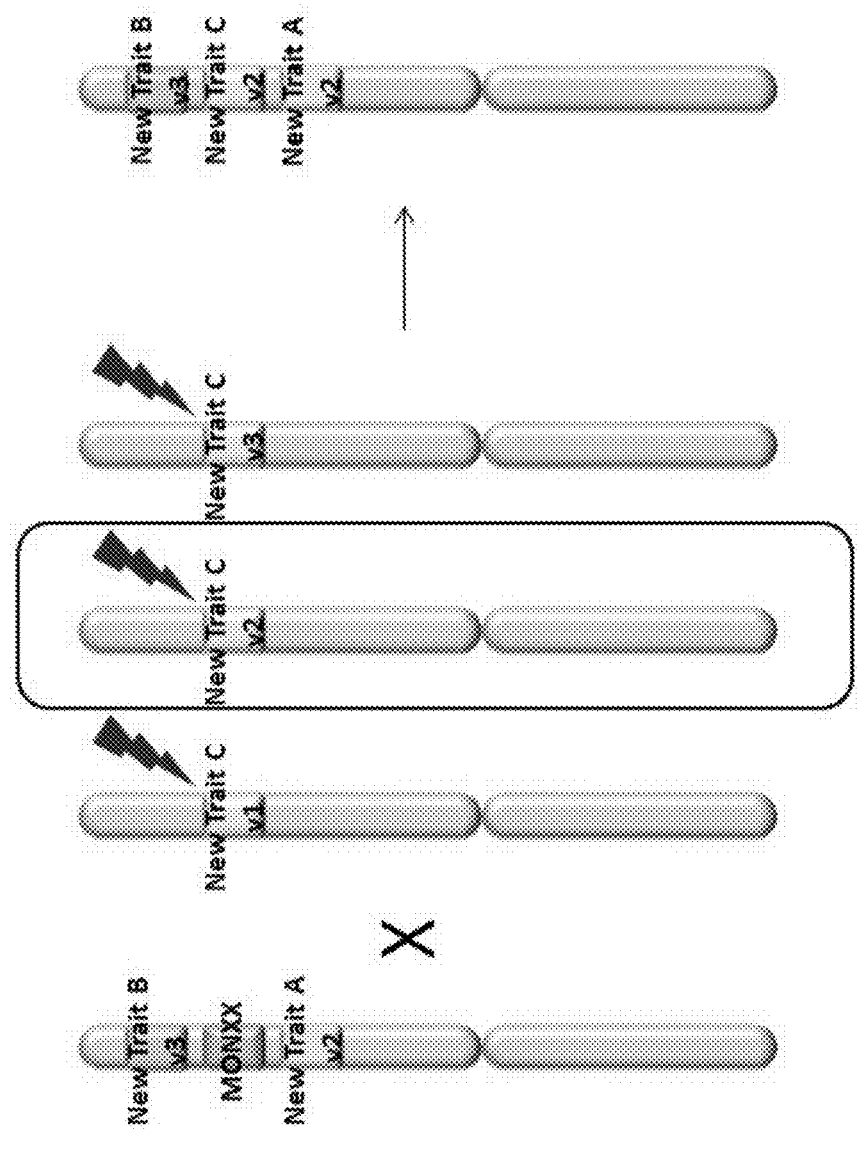
FIG. 3: Shows a schematic of recycling of a desired trait in a megalocus through targeting and recombination.

Once a first recombinant is produced with desired transgenes from both initial parents, these progeny will then be crossed with a third parent harboring additional desired traits to produce further progeny with all of the desired traits. Progeny will then be screened from the hybrid for chromosomes containing both the first and the second blocks of desired transgenes (FIGS. 2 and 3). If desired, a plant containing a single chromosome with all desired transgenes may be selfed and progeny with two or more copies of the chromosome can be produced.

Once one or more plants with all desired transgenes from both blocks of transgenes is obtained and identified, the plant will be crossed with a further plant containing additional desired transgenes. Progeny will be screened as described above to identify plants harboring all desired transgenes from the original blocks and the further parent on a single chromosome. Additional events can be added by repeating these crossing and selection steps.

Once all desired transgenes are incorporated into a single chromosome in cis, the chromosome or megalocus within the chromosome will then be introgressed into a desired line treating the chromosome or megalocus containing multiple transgenes as a single genetic entity. Thus, a plant with all events in cis will effectively segregate as a single locus in the trait integration process.

Example 4

Replacing a Transgene in a Megalocus

Transgenes can be replaced or stacked in different combinations with additional transgenes. As long as no additional supernumerary chromosomes are present or the transgenes are located in a region lacking spontaneous meiotic recombination, all of the loci will segregate as a single genetic unit. Once a megalocus is produced with any number of desired traits, it may then be modified in such a way as to replace a transgene with another desired transgene. As shown in FIG. 3, a plant containing a transgene at a specific locus may be crossed with a plant containing a different transgene at the same locus. After recombination, the new transgene will be present in the megalocus, replacing the transgene found at the same locus that was present in the megalocus before the cross. In this way, new or improved transgenes may be incorporated to replace previous ones. This invention further contemplates the use of additional technology to modulate recombination frequency to increase or decrease recombinants at a given megalocus wherein said technology can be a chemical or environmental (i.e., UV exposure) treatment or a transgenic approach (i.e., modulation of PRDM9 expression).

Example 5

Trait Introgression of Megaloci Comprised of Events that are not Tightly Linked Genetically by Use of One or More Chromosomes with Non-Recombining Regions Sites for event introduction can be selected that are on the same chromosome but are not closely genetically linked if such sites are in a region in which recombination is reduced or eliminated, for instance through chromosome rearrangement. After events are introduced to the selected sites, they can easily be combined onto a single chromosome by induced recombination.

To use chromosomes with blocked recombination in a trait introgression program the following steps are followed:

(1) The non-recombining segment will be introgressed into the desired new lines, as described in the Examples above.

(2) The various traits that have been placed at sites on a chromosome will be introgressed in a region that is part of the non-recombining segment of the chromosome of step 1. Such sites do not need to be selected to be very close genetically.

(3) Plants containing the traits will be crossed to make a hybrid with both traits.

(4) The hybrid will be crossed to a line with the non-recombining segment and screened for individuals with both traits. These progeny plants will be selfed to recover events that are homozygous for both traits, with an expected ration of 1 of 4 homozygous progeny.

(5) The line from step (4) (either the self or plant heterozygous for the non-recombining segment) will be crossed to a line containing a third event to be added.

(6) The hybrid from step (5) will be crossed to the line with the non-recombining segment and screening for individuals with all three traits will be performed. The plant may then be selfed to recover progeny that are homozygous for all three events with an expected ration of 1 of 4 homozygous progeny.

This process will be continued to add many transgenes. In addition, lines with 2 or more traits will be added to other lines with 2 or more traits to quickly pyramid the number of traits added.

What is claimed is:

1. A method for producing a megalocus on a plant B chromosome comprising:
(a) obtaining a hybrid plant comprising a first locus and a second locus, where the first locus is transgenic and the second locus is transgenic, where the first and second loci are located on homologous B chromosomes, and where the loci are at genetically linked positions in said homologous B chromosomes;
(b) crossing the hybrid plant with itself or a distinct plant;
(c) selecting a progeny plant produced from step (b) wherein genetic recombination has occurred between said first locus and said second locus to produce a megalocus comprising the first and second loci arranged in cis, wherein the genetic recombination is not induced recombination; and (d) crossing the progeny plant selected in step (c) to a plant that either lacks B chromosomes or contains B chromosomes with which the B chromosome containing the megalocus is unable to pair.

2. The method of claim 1, further comprising:

(a) obtaining a further hybrid plant comprising said megalocus and a third locus, where the third locus is transgenic, where the megalocus and third locus are located on homologous chromosomes, and wherein the megalocus and third locus are at genetically linked positions in said homologous chromosomes;

(b) crossing the further hybrid plant with itself or a distinct plant; and (c) selecting a further progeny plant produced from step (b) wherein genetic recombination has occurred between said megalocus and said third locus to produce a further megalocus comprising the first, second and third loci arranged in cis, wherein steps (a)-(c) occur prior to step (d).

3. The method of claim 2, wherein steps (a)-(c) are repeated 2 or more times with still further hybrid plants comprising additional loci, where the additional loci are transgenic, to obtain yet a further megalocus comprising the first through third loci and the additional loci arranged in cis.

4. The method of claim 1, wherein obtaining the hybrid plant comprises crossing a first plant comprising the first locus with a second plant comprising the second locus.

5. The method of claim 4, further comprising one or both of (i) transforming said first plant or a progenitor thereof with a transgene to produce said first locus; or (ii) transforming said second plant or a progenitor thereof with a transgene to produce said second locus;

wherein said transforming occurs prior to step (a).

6. The method of claim 5, wherein said transforming comprises site-specific introduction of a transgene to produce the first locus at a position genetically linked with said second locus.

7. The method of claim 1, wherein said progeny plant produced from step (b) is hemizygous for said megalocus.

8. The method of claim 1, wherein said progeny plant produced from step (b) is homozygous for said megalocus.

9. The method of claim 1, wherein said megalocus is introgressed into a plant of the same variety as said first plant or a distinct variety from said first plant.

10. The method of claim 9, wherein said introgression comprises a haploid induction cross.

11. The method of claim 1, wherein said megalocus is introgressed into a plant of a distinct species from said first plant.

* * * * *